United States Patent [19]

Goseki

[11] Patent Number: 5,513,658
[45] Date of Patent: May 7, 1996

[54] KNEE SUPPORTER

[75] Inventor: Makoto Goseki, Osaka, Japan

[73] Assignee: Morito Kabushiki Gaisha, Osaka, Japan

[21] Appl. No.: 413,701

[22] Filed: Mar. 30, 1995

[30] Foreign Application Priority Data

Mar. 30, 1994 [JP] Japan .................... 6-061043

[51] Int. Cl.$^6$ ............................. A61F 5/37; A61F 5/00
[52] U.S. Cl. .......................... 128/882; 602/23; 602/26
[58] Field of Search .......................... 128/846, 882; 602/5, 23, 26, 60, 61, 62, 63

[56] References Cited

U.S. PATENT DOCUMENTS

| | | | |
|---|---|---|---|
| 4,651,722 | 3/1987 | Karczewski | 602/26 |
| 4,724,831 | 2/1988 | Huntjens | 602/26 |
| 5,086,761 | 2/1992 | Ingram | 602/26 |
| 5,139,476 | 8/1992 | Peters | 602/26 |
| 5,385,538 | 1/1995 | Mann | 602/26 |
| 5,399,153 | 3/1995 | Caprio | 602/26 |

Primary Examiner—Michael A. Brown
Attorney, Agent, or Firm—Armstrong, Westerman, Hattori, McLeland & Naughton

[57] ABSTRACT

A knee supporter comprising: a supporter body 3 made of a cloth having excellent hygroscopicity and stretchability and formed with swathing ears 2 by bifurcating the righthand and lefthand end portions of a knee-back abutting portion 1; an air-permeable cloth member 4 made of net and fixed over the surface of the knee-back abutting portion 1; two fastening members 5 made of a cloth having excellent stretchability and a piled surface, the fastening members being given the same shape as that of the swathing ears 2 and fixed over the surfaces of the swathing ears 2; and a knee-cap covering band 6 made stretchable and sewn along one of the boundaries between the fastening members 5 and the air-permeable cloth member 4. The supporter body 3, the air-permeable cloth member 4, the two fastening members 5 and the knee-cap covering band 6 are combined to form over-knee fastening bands 7 and under-knee fastening bands 8 at the righthand and lefthand sides of the knee supporter.

7 Claims, 3 Drawing Sheets

KNEE SUPPORTER

BACKGROUND OF THE INVENTION

1. Field of the Invention

The present invention relates to a knee supporter to be used for swathing a knee in orthopedics so that it may aid the bends of the knee and may warm and protect the knee.

2. Prior Art

The knee supporter of the prior art is constructed by sewing such a face fastener male member to the back of one longitudinal end portion of a band body, which has a width sufficient for covering the cap of the knee and above and below the knee and a length sufficient for swathing the knee and which has a piled surface, as can be removably fastened to that piled surface. The knee supporter thus constructed is used by swathing the knee in it while pulling it in its stretching direction with and exposing the piled surface to the outside and by fastening the face fastener male member of the one end portion back to the piled surface to keep the swathing state.

In case the aforementioned knee supporter of the prior art is used to swath the knee, it can warm and protect the knee, as expected. However, the knee supporter grows hot and stuffy, as it is used, to given an uncomfortable feeling and obstructs the bends of the knee so that it gives inconveniences in walking and going upstairs and downstairs. Still the worse, the knee supporter swathes all the knee portions including the cap portion, the over-knee portion and the under-knee portions having different thicknesses so that its fastening degree becomes different in the individual knee portions to give a feeling of physical disorder. Another problem to be solved resides in that the knee supporter is liable to slip from its swathing position.

SUMMARY OF THE INVENTION

The present invention has an object to provide a knee supporter which can improve the air-permeability and aid the bends of the knee while keeping its intrinsic functions to warm and protect the knee and which can swathe the knee while fitting the different thicknesses of the knee portions to lighten the feeling of physical disorder and can ensure stable swathing without any slip.

According to the present invention, there is provided a knee supporter comprising: a supporter body made of a cloth having excellent hygroscopicity and stretchability and formed with swathing ears by bifurcating the righthand and lefthand end portions of a knee-back abutting portion; an air-permeable cloth member made of net and fixed over the surface of said knee-back abutting portion; two fastening members made of a cloth having excellent stretchability and a piled surface, said fastening members being given the same shape as that of said swathing ears and fixed over the surfaces of said swathing ears; a knee-cap covering band made stretchable and sewn along one of the boundaries between said fastening members and said air-permeable cloth member, said supporter body, said air-permeable cloth member, said two fastening members and said knee-cap covering band being combined to form over-knee fastening bands and under-knee fastening bands at the righthand and lefthand sides of said knee supporter; auxiliary stop members sewn to the back of the free end portion of one of said righthand and lefthand swathing ears and made of such face fastener male members as can be removably attached to said piled surface; at least one knee-bend aiding elastic member sewn to said two fastening members along such knee bending lines as can bend out with respect to the boundaries between said fastening members and said air-permeable cloth member; and a main stop member sewn to the back of the free end portion of said knee-cap covering band and made of such a face fastener male member as can be removably attached to said filed surface.

The knee supporter thus constructed is applied to bring its knee back abutting portion into abutment against the knee back such that its air-permeable cloth member is exposed to the outside. After this, the righthand and lefthand over-knee fastening bands are pulled around and are properly fastened over the knee cap. Then, the auxiliary stop members at the back of one over-knee fastening band are fastened to the filed surface of the other over-knee fastening band. Next, the under-knee fastening bands are pulled around and are fastened like the over-knee fastening bands under the knee cap. Finally, the knee-cap covering band is pulled to over the knee cap and is properly fastened. After this, the main stop member sewn on the back of the free end portion of the knee-cap covering band is fastened to the piled surfaces of the over-knee and under-knee fastening bands. Thus, the knee is swathed in the knee supporter.

As a result, when the knee is swathed in the knee supporter of the present invention, the air-permeable cloth portion can reserve the air-permeability in the knee back which is the most liable to become hot and stuffy. The knee-bend aiding elastic members are arranged to abut along the bending lines formed at the two sides of the knee so that they act to aid the knee in bending. Moreover, the over-knee fastening bands, the under-knee fastening bands and the knee-cap covering band can properly fasten and fix the knee portions having different thicknesses while adjusting them individually, to lighten the feeling of physical disorder in wearing the knee supporter so that the knee can be swathed stably without any slip. Thus, the present invention can provide a knee supporter which can improve the air-permeability and aid the bends of the knee while warming and protecting the knee and which can swathe the knee while fitting the different thicknesses of the knee portions to lighten the feeling of physical disorder and can ensure stable swathing without any slip.

DESCRIPTION OF THE PREFERRED EMBODIMENT

Figure 1:
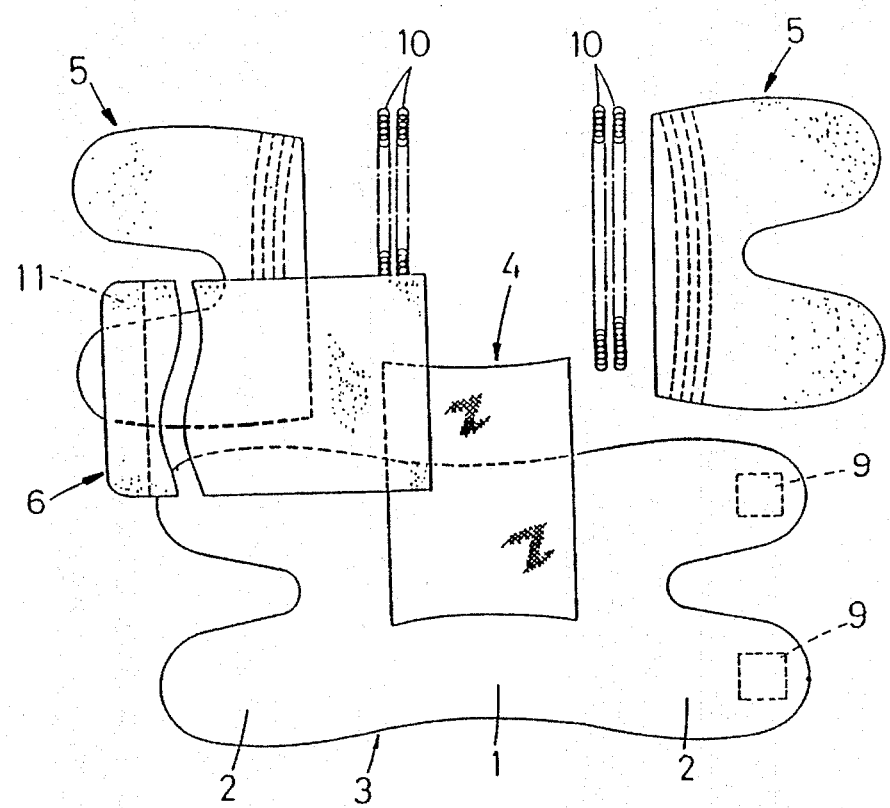
FIG. 1 is an exploded top plan view showing a knee supporter according to an embodiment of the present invention.
Figure 2:
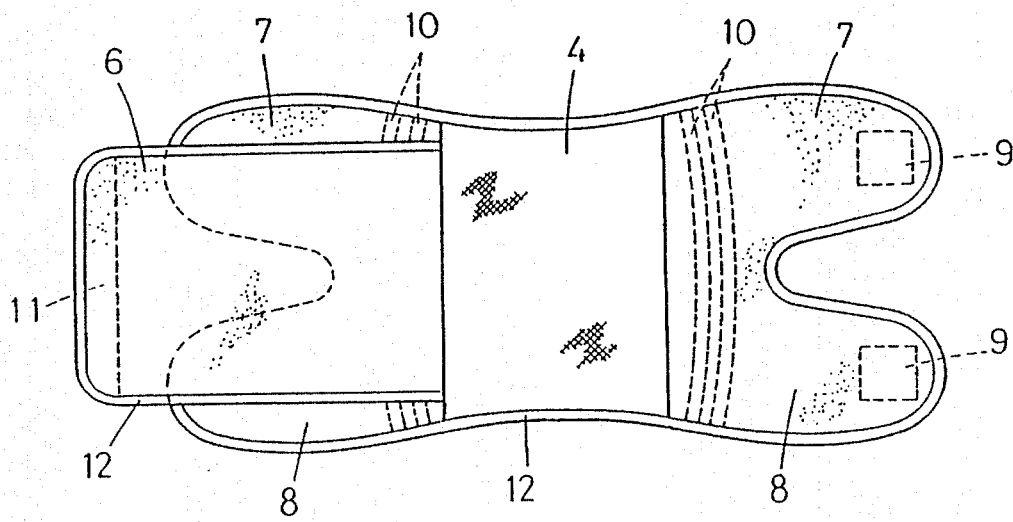
FIG. 2 is a top plan view showing a completed product of the knee supporter.
Figure 3:
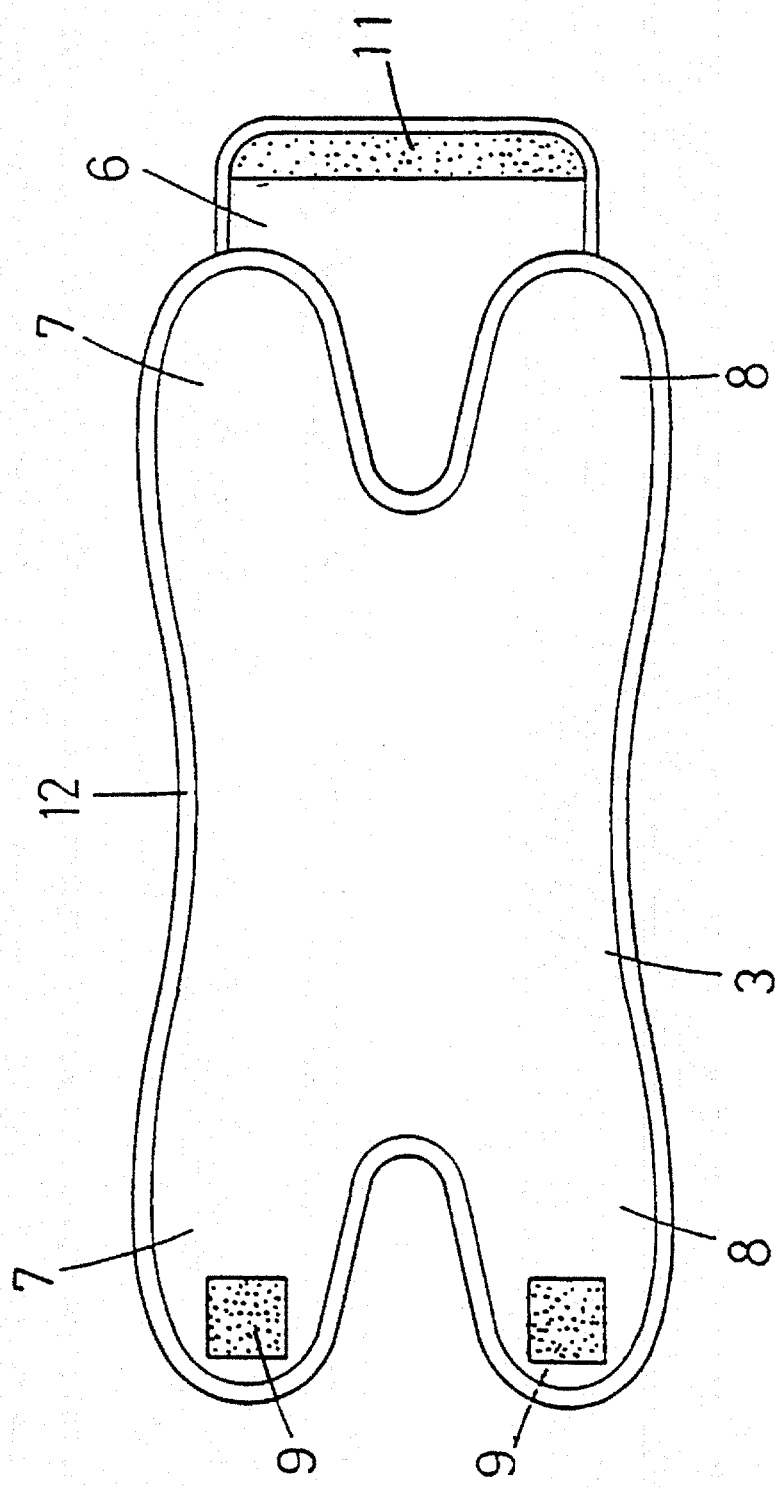
FIG. 3 is a back view showing the completed product.
Figure 4:
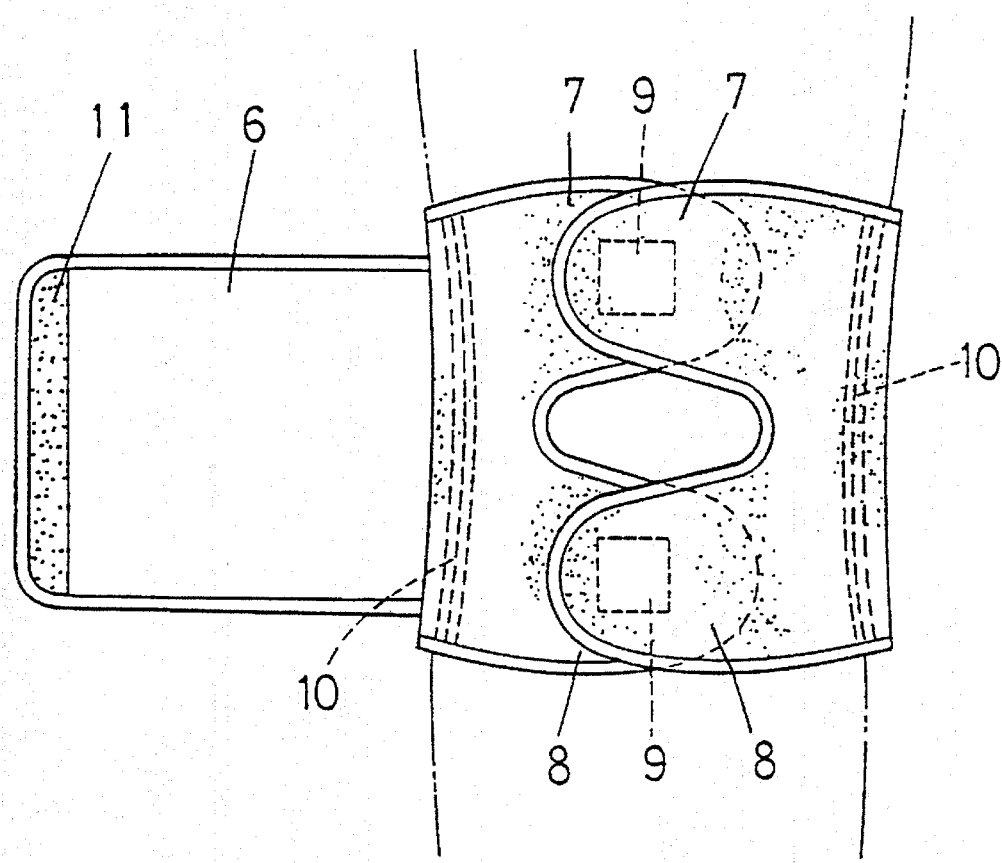
FIG. 4 is a front elevation showing the state in which the knee supporter swathes a knee.

A knee supporter according to the present invention is constructed to comprise: a supporter body 3 made of a cloth of cotton fibers having excellent hygroscopicity and stretchability and formed with swathing ears 2 by bifurcating the righthand and lefthand end portions of a knee-back abutting portion 1; an air-permeable cloth member 4 made of net and fixed over the surface of the knee-back abutting portion 1; two fastening members 5 made of a cloth of nylon fibers having excellent stretchability and a piled surface, given the same shape as that of the swathing ears 2 and fixed over the surfaces of the swathing ears 2; a knee-cap covering band 6 made of nylon fibers having stretchability and sewn along one of the boundaries between the fastening members 5 and the air-permeable cloth member 4. The supporter body 3, the air-permeable cloth member 4, the two fastening members 5 and the knee-cap covering band 6 are thus combined to form over-knee fastening bands 7 and under-knee fastening bands 8 at the righthand and lefthand sides of the knee supporter.

To the backs of the free end portions of the righthand or lefthand swathing ears 2, moreover, there are sewn auxiliary stop members 9 which are made of such face fastener male members as can be removably attached to the pile surface of the corresponding fastening member 5. In the two fastening members 5, there are sewn individually two knee-bend aiding elastic members 10 which extend along such knee bending lines as will bend out with respect to the boundaries between the fastening members 5 and the air-permeable cloth member 4. To the back of the free end portion of the knee-cap covering band 6, moreover, there is sewn a main stop member 11 which is made of such a face fastener male member as can be removably attached to the filed surface of the corresponding fastening member 5.

The knee-bend aiding elastic members 10 may be made of any elastic material such as a synthetic resin of polypropylene if it can aid the bends of the knee, but may preferably be made of a spiral core material of stainless steel because of its high righting force and corrosion-resistance.

Moreover, the two overlapped portions and the knee-cap covering band 6 may preferably have their peripheral edges hemmed with hemming cloths of nylon fibers having stretchability so as to prevent the fray and to improve the appearance.

Still moreover, the heat retaining properties of the knee cap can be better improved by backing the knee-cap covering band 6 with either a cloth of fibers containing ceramics for irradiating far infrared rays or a cloth coated with ceramic powder for irradiating far infrared rays.

Incidentally, the knee-bend aiding elastic members 10 are fixedly sewn in the foregoing embodiment. In order to extract the elastic members 10 when the knee supporter is to be washed, pockets having their one-side ends opened can be formed along the knee bending lines to hold the knee-bend aiding elastic members 10 therein.

The knee supporter thus constructed is manufactured in the following procedure. At first, the air-permeable cloth member 4 is sewn over the surface of the knee back abutting portion 1 of the supporter body 3 which is cut to have such a contour as is prepared by bifurcating the righthand and lefthand end portions of the knee back abutting portion 1 to form the swathing ears 2. After this, the two fastening members 5, which are cut to the same shape as the swathing ears 2 and prepared by sewing the knee-end aiding elastic members 10, are sewn over the swathing ears 2, i.e., the righthand and lefthand margins of the supporter body 1 prepared by sewing the air-permeable cloth member 4. Then, the supporter body is completed by having its peripheral edge hemmed with the cloth 12.

Then, the knee-cap covering band 6 is cut to have its peripheral edge hemmed with the cloth 12 and has its free end portion back sewn with the main stop member 11.

Finally, the knee-cap covering band 6 thus prepared has its base end portion sewn to the supporter body along one of the boundaries between the fastening members 5 and the air-permeable cloth member 4, to manufacture the knee supporter.

This knee supporter is applied to bring its knee back abutting portion 1 into abutment against the knee back such that its air-permeable cloth member 4 is exposed to the outside. After this, the righthand and lefthand over-knee fastening bands 7 are pulled around and are properly fastened over the knee cap. Then, the auxiliary stop members 9 at the back of one over-knee fastening band 7 are fastened to the filed surface of the other over-knee fastening band 7. Next, the under-knee fastening bands 8 are pulled around and are fastened like the over-knee fastening bands 7 under the knee cap. Finally, the knee-cap covering band 6 is pulled to over the knee cap and is properly fastened. After this, the main stop member 11 sewn on the back of the free end portion of the knee-cap covering band 6 is fastened to the piled surfaces of the over-knee and under-knee fastening bands 7 and 8. Thus, the knee is swathed in the knee supporter.

What is claimed is:

1. A knee supporter comprising: a supporter body 3 made of a cloth having excellent hygroscopicity and stretchability and formed with swathing ears 2 by bifurcating the righthand and lefthand end portions of a knee-back abutting portion 1; an air-permeable cloth member 4 made of net and fixed over the surface of said knee-back abutting portion 1; two fastening members 5 made of a cloth having excellent stretchability and a piled surface, said fastening members being given the same shape as that of said swathing ears 2 and fixed over the surfaces of said swathing ears 2; a knee-cap covering band 6 made stretchable and sewn along one of the boundaries between said fastening members 5 and said air-permeable cloth member 4, said supporter body 3, said air-permeable cloth member 4, said two fastening members 5 and said knee-cap covering band 6 being combined to form over-knee fastening bands 7 and under-knee fastening bands 8 at the righthand and lefthand sides of said knee supporter; auxiliary stop members 9 sewn to the back of the free end portion of one of said righthand and lefthand swathing ears 2 and made of such face fastener male members as can be removably attached to said piled surface; at least one knee-bend aiding elastic member 10 sewn to said two fastening members 5 along such knee bending lines as can bend out with respect to the boundaries between said fastening members 5 and said air-permeable cloth member 4; and a main stop member 11 sewn to the back of the free end portion of said knee-cap covering band 6 and made of such a face fastener male member as can be removably attached to said filed surface.

2. A knee supporter according to claim 1, wherein said knee-bend aiding elastic member 10 is made of a spiral core member of stainless steel.

3. A knee supporter according to claim 1, wherein the cloth making said supporter body 3 and having excellent hygroscopicity and stretchability is made of cotton.

4. A knee supporter according to claim 1, wherein the stretchable cloth making said fastening members 5 and said knee-cap covering band 6 is made of nylon.

5. A knee supporter according to claim 1, wherein said two overlapped portion and said knee-cap covering band 6 have their peripheral edges hemmed with a stretchable cloth.

6. A knee supporter according to claim 1, wherein said knee-cap covering band 6 has its back made of a cloth of fibers containing ceramics for irradiating far infrared rays.

7. A knee supporter according to claim 1, wherein said knee-cap covering band 6 has its back made of a cloth coated with ceramic powder for irradiating far infrared rays.

* * * * *